United States Patent
Guan et al.

(10) Patent No.: US 10,240,148 B2
(45) Date of Patent: *Mar. 26, 2019

(54) METHODS AND COMPOSITIONS FOR PREVENTING CONCATEMERIZATION DURING TEMPLATE-SWITCHING

(71) Applicant: New England Biolabs, Inc., Ipswich, MA (US)

(72) Inventors: Shengxi Guan, Stoneham, MA (US); Thomas C. Evans, Jr., Topsfield, MA (US); Nicole Nichols, Reading, MA (US); Yanxia Bei, Boxford, MA (US)

(73) Assignee: New England Biolabs, Inc., Ipswich, MA (US)

( * ) Notice: Subject to any disclaimer, the term of this patent is extended or adjusted under 35 U.S.C. 154(b) by 251 days.

This patent is subject to a terminal disclaimer.

(21) Appl. No.: 15/240,166

(22) Filed: Aug. 18, 2016

(65) Prior Publication Data
US 2018/0037884 A1 Feb. 8, 2018

Related U.S. Application Data

(60) Provisional application No. 62/370,469, filed on Aug. 3, 2016.

(51) Int. Cl.
*C12Q 1/68* (2018.01)
*C12N 15/10* (2006.01)
(Continued)

(52) U.S. Cl.
CPC ....... *C12N 15/1096* (2013.01); *C12N 9/1276* (2013.01); *C12Q 1/6806* (2013.01); *C12Q 1/6848* (2013.01); *C12Y 207/07049* (2013.01)

(58) Field of Classification Search
CPC ............ C12Q 1/6806; C12Q 2521/107; C12Q 2521/301; C12Q 2525/131;
(Continued)

(56) References Cited

U.S. PATENT DOCUMENTS

| 5,962,272 A | 10/1999 | Chenchik et al. |
| 9,012,183 B2 | 4/2015 | Lambowitz et al. |

(Continued)

FOREIGN PATENT DOCUMENTS

| WO | WO 2012/116146 | 8/2012 |
| WO | WO2014-201273 | 12/2014 |
| WO | WO 2015/094861 | 6/2015 |

OTHER PUBLICATIONS

Kapteyn et al. "Incorporation of non-natural nucleotides into template-switching oligonucleotides reduces background and improves cDNA synthesis from very small RNA samples." BMC Genomics, Jul. 2, 2010 (Jul. 2, 2010), vol. 11, pp. 1-9.
(Continued)

*Primary Examiner* — Teresa E Strzelecka
(74) *Attorney, Agent, or Firm* — New England Biolabs, Inc; Harriet M. Strimpel

(57) ABSTRACT

Compositions and methods for performing a template-switching reaction are provided that may include reducing or eliminating concatemerization of the template-switching oligonucleotide (TSO). In some embodiments, the composition may comprise: a reverse transcriptase; a TSO that includes a recognition sequence for a site-specific double strand nucleic acid cleaving enzyme, wherein the TSO has at its 3' end at least one nucleotide capable of hybridizing to at least one or more non-templated nucleotides added to a templated cDNA strand by the reverse transcriptase; and a site-specific double strand nucleic acid cleaving enzyme that cleaves the TSO at the recognition sequence.

31 Claims, 8 Drawing Sheets

(51) Int. Cl.
   *C12N 9/12*   (2006.01)
   *C12Q 1/6806* (2018.01)
   *C12Q 1/6848* (2018.01)
   *C07H 21/04*  (2006.01)

(58) Field of Classification Search
   CPC ........ C12Q 2525/151; C12Q 2525/155; C12Q 1/6848; C12N 15/1096; C12N 9/1276; C12Y 207/07049
   See application file for complete search history.

(56) References Cited

U.S. PATENT DOCUMENTS

2014/0113332 A1   4/2014   Betts et al.
   2015/0111789 A1   4/2015   Betts et al.
   2015/0203906 A1*  7/2015   Betts .................... C12Q 1/6869
                                                         435/6.12

OTHER PUBLICATIONS

Bibillo et al. "End-to-End Template Jumping by the Reverse Transcriptase Encoded by the R2 Retrotransposon," The Journal of Biological Chemistry, Apr. 9, 2004 (Apr. 9, 2004), vol. 279, No. 15, pp. 14945-14953.

International Search Report for International application No. PCT/US2017/044509 dated Oct. 5, 2017.

Saliba, et al., Single-cell RNA-seq: advances and future challenges, Nucleic Acids Research, doi:10.1093/nar/gku555 (2014).

Enyeart, et al., Biotchnological application of mobile group II introns and their reverse trascriptases: gene targeting, RNA-seq, and non-coding RNA analysis, Mobile DNA, 5:2 (2014).

Turchinovich, et al., An ultrasensitive ligation-independent method for generating of DNA libraries for deep sequencing from picogram amounts of DNA and RNA, RNA Biology, 11(7): 817-828 (2014).

Patel, et al., Marked infidelity of human immunodeficiency virus type 1 reverse transcriptase at RNA and DNA template ends, Proc Natl Acad Sci USA, 91(2):549-53 (1994).

Golinelli, et al., Nontemplated Base Addition by HIV-1 RT Can Induce Nonspecific Strand Transfer in Vitro, Virology, 294(1):122-34 (2002).

Chen, et al., Reverse Transcriptase Adds Nontemplated Nucleotides to cDNAs During 5'-Race adn Primer Extension, Biotechniques, 30(3):574-80, 582 (2001).

Zajac, et al., Base Preferences in Non-Templated Nucleotide Incorporation by MMLV-Derived Reverse Transcriptases, PLOS one (2013).

* cited by examiner

| Oligo Function | Features | How it works |
|---|---|---|
| cDNA Primer | Radom primer containing adaptor | |
| | Poly (dT) primer containing adaptor | |
| | Gene Specific primer | |
| | Poly (dT) primer containing molecular ID and adaptor | |
| | Gene Specific containing molecular ID and adaptor | |
| Template Switching Oligo | Template Switching Oligo | |
| | Template Switching Oligo incorporating Molecular ID | |
| | Template Switching Oligo incorporating sequencing platform adaptors | |
| PCR Primer | Primer recognizing cDNA primer adaptor and template switching oligo | |
| | Primer with sequencing platform adaptors attached | |

FIG. 7

METHODS AND COMPOSITIONS FOR PREVENTING CONCATEMERIZATION DURING TEMPLATE-SWITCHING

CROSS-REFERENCE

This application claims the benefit of U.S. provisional application Ser. No. 62/370,469, filed Aug. 3, 2016 herein incorporated by reference herein.

BACKGROUND

One step in RNA sequencing (RNA-Seq) is amplification of template RNA against a background of ribosomal RNA. Amplification may involve adapter ligation and since ligation is non-specific, it is desirable to introduce target enrichment by some means. One method takes advantage of the template-switching activity of reverse transcriptase (see for example, U.S. Pat. No. 5,962,272).

One problem of template-switching is that oligonucleotides designed to hybridize with the 3' end of the reverse transcriptase synthesized first strand cDNA also can form concatemers with each other as the reverse transcriptase switches between templated and non-templated DNA synthesis. This can cause non-specific background and wasted, and therefore costly, sequencing capacity.

Template-switching methods can be applied to the analysis of the transcriptome of single cells to provide gene expression information for use in cell biology studies and disease diagnostics. The initial step in obtaining the transcriptome of a single cell is the isolation of individual cells from a potentially heterogeneous population. This has been described for example, in Saliba, et al., Nucleic Acids Research, 1 doi: 10.1093/nar/gku555 (2014).

Most tissues contain a large number of cell types with distinct lineage, where each cell type contributes to the functioning of the tissue. To understand the relationship among different cell types, single-cell analysis can provide not only genomic information but also transcript information derived from sequencing of mRNA. Studying cells at the single-cell level offers unique opportunities to dissect the interplay between intrinsic cellular processes and extrinsic stimuli such as the local environment or neighboring cells in cell fate determination and can be used to identify cell lineages. Single cell RNA-Seq finds many uses such as, for example, cell lineage analysis; effect of external stimuli on cells, analyzing tissue heterogeneity in cancer biopsies; discovery of rare cells in liquid biopsies; and analyzing nucleic acid content of exosomes.

RNA-Seq has also facilitated the annotation of prokaryotic genomes by defining 5' and 3' untranslated regions of mRNAs and discovered many previously unrecognized RNA molecules including an unexpected degree of genome-wide antisense transcription.

The reduction of background and the minimization of unnecessary sequencing would enable RNA-Seq to be more sensitive and cost effective.

SUMMARY

In general, a composition is provided that includes: (a) a template-switching oligonucleotide (TSO) comprising a recognition sequence for a site-specific nucleic acid cleaving enzyme, wherein the TSO has at its 3' end at least one nucleotide that is complementary to one or more non-template nucleotides at the 3' end of a cDNA strand of a RNA-cDNA complex; (b) a reverse transcriptase; and (c) a site-specific nucleic acid cleaving enzyme that recognizes the recognition sequence in the TSO. In one aspect, the composition further includes an RNA template where for example, the RNA template is purified or comes from a cell lysate or from another source. For example, the RNA template may be obtained from a cell lysate of a single cell or a small number of cells (less than 1000 cells, 500 cells or 100 cells). The RNA template may be total RNA, micro RNA, long non-coding RNA, exome RNA, gene silencing RNA or any other RNA of interest in a sample to be analyzed. For example, the RNA template may be poly A+RNA. The RNA template may be obtained from a vertebrate, invertebrate, plant or prokaryotic source. For example the RNA template may be obtained from a mammal. The RNA template may include a 5' modified GMP cap such as a 7-methylguanosine or an affinity tag-labeled GMP cap.

In one aspect, the composition includes a cDNA synthesis primer. The cDNA synthesis primer may be an oligo(dT) primer, a random primer, or a transcript-specific primer. In another aspect, the composition includes a cDNA synthesis primer having a 5' tail that does not hybridize to the RNA template.

In one aspect, the TSO may be part DNA and part RNA to form a DNA-RNA synthon. The TSO may include an amplification primer sequence, and/or optionally a molecular barcode sequence, between the recognition sequence for the site-specific nucleic acid cleaving enzyme and the at least one or more 3'-terminal nucleotides. In one aspect, the TSO comprises three riboguanine residues at its 3' end.

In one aspect, the reverse transcriptase is Moloney murine leukemia virus reverse transcriptase (M-MLV RT), M-MLV reverse transcriptase (M-MLV RT) lacking RNaseH activity (or having reduced RNaseH activity), human T-cell leukemia virus type I (HTLV-I) reverse transcriptase, bovine leukemia virus (BLV) reverse transcriptase, Rous sarcoma virus (RSV) reverse transcriptase, or human immunodeficiency virus (HIV) reverse transcriptase, or a variant thereof. In one aspect the reverse transcriptase is a M-MLV RT having reduced or no RNaseH activity.

In one aspect, the site-specific nucleic acid cleaving enzyme is a restriction endonuclease where optionally, the restriction endonuclease is active at a temperature in the range of 35° C. to 55° C. and is capable of inactivation by incubation at a temperature of at least 65° C. for a period of 10 minutes.

In general, a method is provided for making cDNA that comprises incubating a composition as defined herein with an RNA template under conditions (that may include a temperature of 35° C. to 55° C. for a period of at least 30 minutes) so as to produce cDNA molecules that comprise, at the 3' end, at least one non-template nucleotide that hybridizes with the 3' end of the TSO wherein, during incubation, the site-specific nucleic acid cleaving enzyme prevents concatemer formation. In one aspect, the method comprises the initial step of forming a reaction mix by combining the composition with the RNA template, prior to the incubation step. Optionally, the method comprises an additional step of amplifying the cDNA molecules generated in the incubation step to produce amplification products. The amplification may be done by PCR using a first primer and a second primer. The first primer may hybridize to a sequence at the 3' end of the cDNA and/or the second primer may hybridize to a sequence at the 5' end of the cDNA that is the complement of a sequence in the adapter-oligo dT primer. Optionally, the method comprises the step of sequencing the amplification products, following the amplification step.

In another aspect, the reverse transcriptase and the site-specific nucleic acid cleaving enzyme may be inactivated by incubating the reaction mix at a temperature of at least 65° C. for a period of at least 10 minutes.

In one aspect, the RNA template is from a clinical sample such as fetal cells in maternal blood, immune cells responding to a foreign body or cancer cells from a tumor.

In one aspect of the method, the site-specific nucleic acid cleaving enzyme is a sequence specific double strand (ds) DNA cleaving enzyme. Examples include: a restriction enzyme, an N-glycosylase, a lyase (N-glycosylase-lyase), an endonuclease, a cas9 ortholog, and Argonaut ortholog.

(1) A mRNA is shown having a polyA tail. An oligonucleotide primer (generally a DNA) with known sequence (Adapter-Oligo dT) hybridizes to the mRNA through the polyA tail and primes the reverse transcriptase. The reverse transcriptase synthesizes a first strand cDNA along the mRNA to the 5' end of the mRNA. In this example, the reverse transcriptase adds a non-templated dCdCdC to the cDNA product at its 3' end.

(2) A synthetic TSO is designed with a 3'-terminal nucleotide sequence, here exemplified by rGrGrG, which can anneal to the sequence added by non-template addition at the 3' end of the cDNA. The reverse transcriptase then switches from copying the mRNA to copying the TSO.

(3) PCR primers complementary to part or all of the two known adapter sequences are then added to the reaction to amplify the cDNA.

Figure 2:
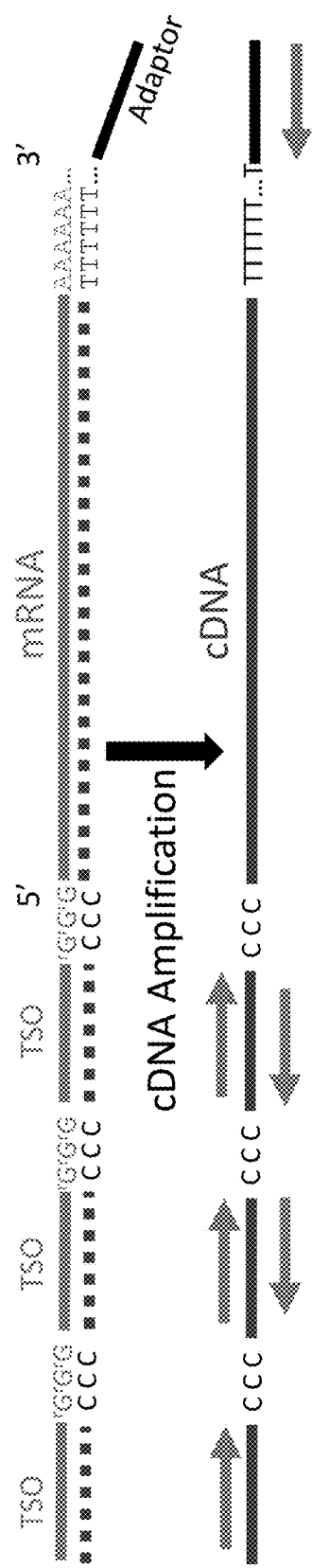

FIG. 2 shows a schematic illustration of concatemer formation that occurs during template-switching by the reverse transcriptase. Once the reverse transcriptase copies to the end of a TSO it adds non-templated nucleotides, a run of dC's in this example, that can hybridize with another TSO that the reverse transcriptase can use as a substrate. In this manner, concatemers of TSO sequences are generated. During PCR, PCR primers anneal to each TSO in the concatemer to produce amplicons of various lengths some of which include amplicons of the concatemer and not the cDNA.

Figure 3:
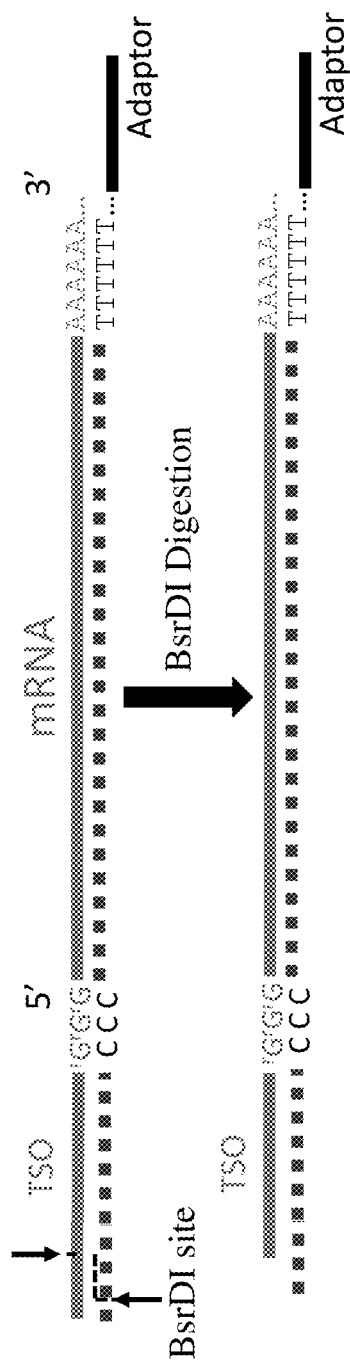

FIG. 3 shows a schematic representation of cleavage of the TSO with a site-specific DNA cleavage enzyme, here exemplified by a restriction enzyme, BsrDI. A cleavage site is designed and introduced into the TSO at its 5' end and the cleavage enzyme is added to the reaction mixture during the reverse transcription step, which is prior to amplification. The cleavage enzyme removes or prevents concatemers by cleavage of double stranded DNA at a position at the 5' end of the TSO. The reaction conditions were an incubation with reverse transcriptase and the cleavage enzyme (BsrdI) at 42° C. for 90 mins followed by an incubation at 70° C. for 10 mins to inactivate the reverse transcriptase and the cleavage enzyme.

Figure 4:
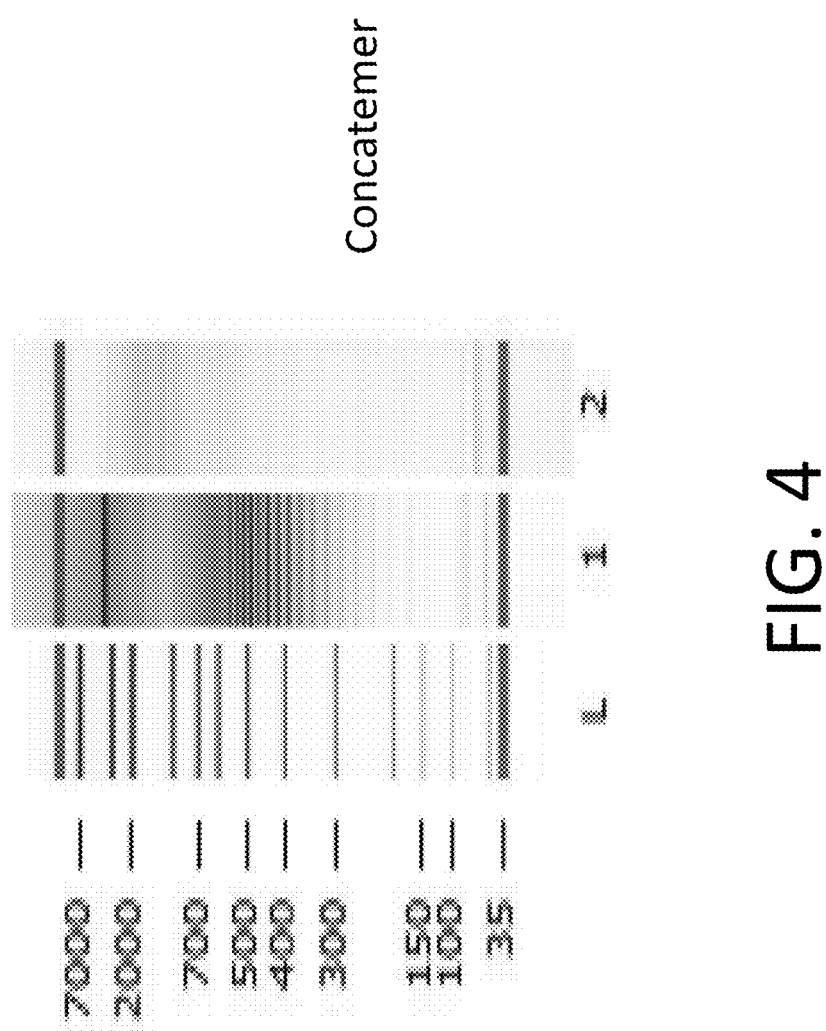

FIG. 4 shows a virtual gel from a Bioanalyzer® (Agilent, Santa Clara, Calif.) trace of an mRNA library prepared using template-switching where the TSO contains a recognition sequence for a site-specific nucleic acid cleaving enzyme. In this instance the site-specific nucleic acid cleaving enzyme is a restriction endonuclease here exemplified by BsrDI.

Lane 1 shows the results with background contamination caused by concatemers in the absence of a restriction endonuclease and lane 2 shows the effect of restriction endonuclease cleavage removing background.

Figure 5:
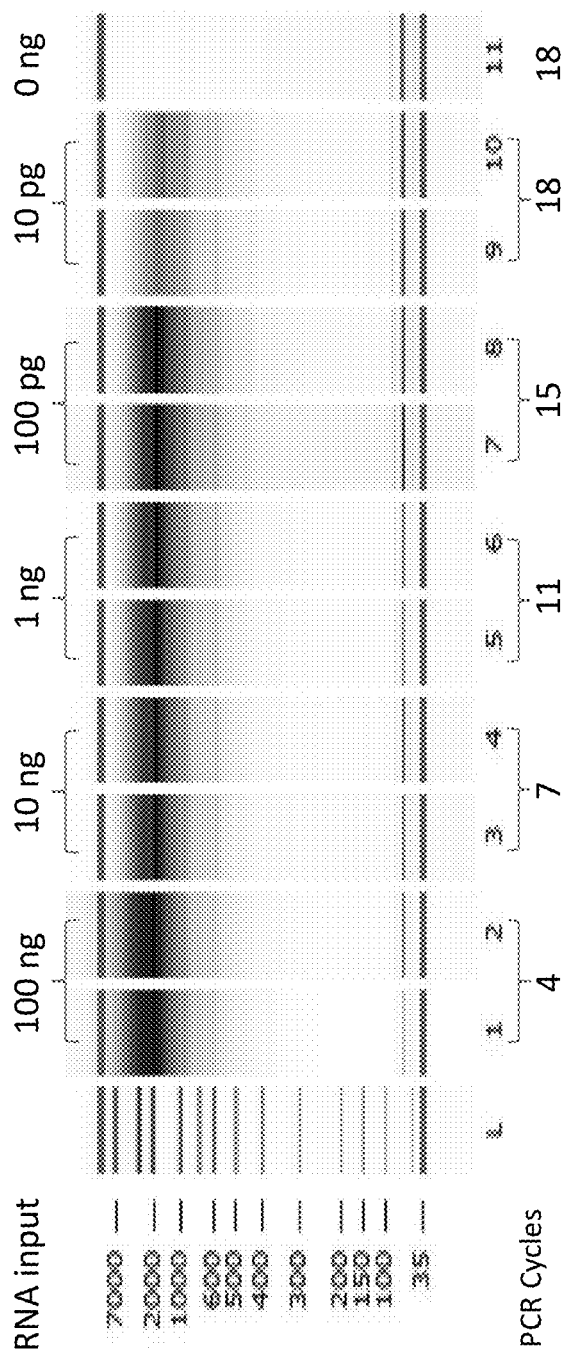

FIG. 5 shows that nucleic acid concentration is not a limiting factor as bands can be detected from as little as 10 pg of total RNA (Universal human reference RNA (Agilent, Santa Clara, Calif.)).

Lane 1 and 2 are duplicates of 100 ng total RNA input. The cDNA library was amplified 4 cycles.

Lane 3 and 4 are duplicates of long total RNA input. The cDNA library was amplified 7 cycles.

Lane 5 and 6 are duplicates of Dig total RNA input. The cDNA library was amplified 11 cycles.

Lane 7 and 8 are duplicates of 100 pg total RNA input. The cDNA library was amplified 15 cycles.

Lane 9 and 10 are duplicates of 10 pg total RNA input. The cDNA library was amplified 18 cycles.

Lane 11 is a negative control with no total RNA input.

Figure 6:
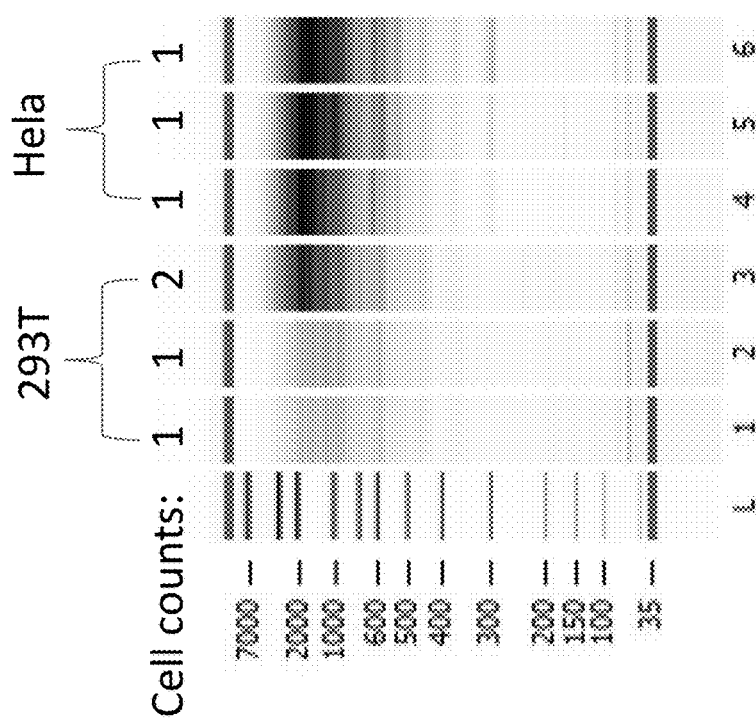

FIG. 6 shows the results of cDNA libraries with starting material of single cell or two cells (293T or Hela cells).

Lane 1, 2 and 3 are cDNA libraries with 1, 1 and 2 293T cells, respectively.

Lane 4, 5 and 6 are cDNA libraries with 1, 1, and 1 Hela cell, respectively.

FIG. 7 shows examples of features that may be included in Adapter-oligo dT and/or the TSO, including adaptor sequences, primer sequences, sample barcode, unique identifier and oligo dT sequences.

Figure 8:
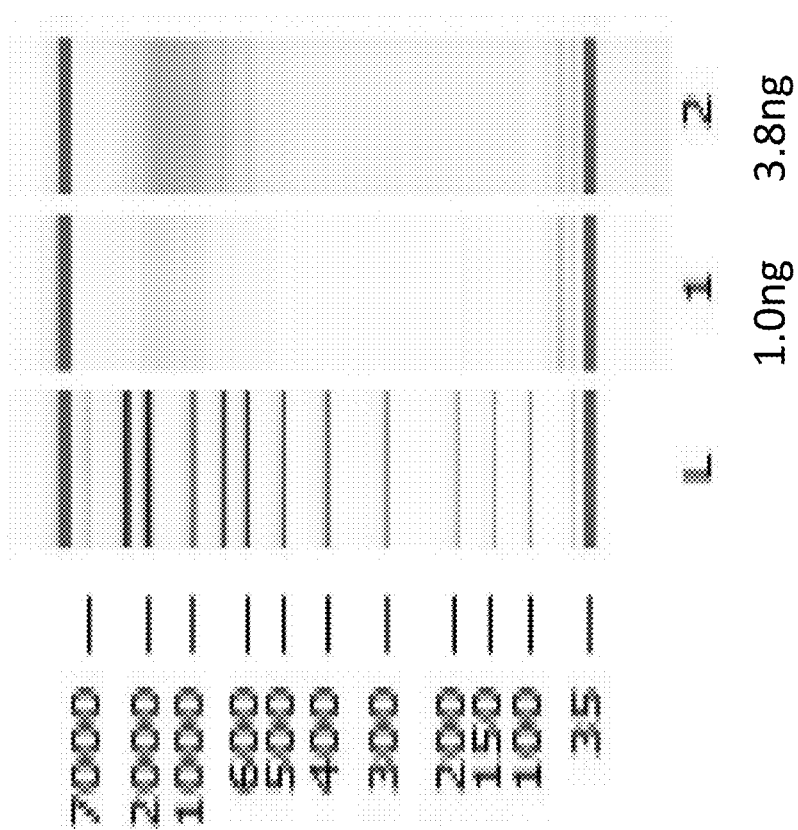

FIG. 8 shows Bioanalyzer analysis of cDNA library prepared by template-switching from mRNA where the TSO contains a site-specific double strand nucleic acid cleavage sequence, without and with a crowding agent Lane 1: without crowding agent, library yield is 1.0 ng; and Lane 2: with the crowding agent, library yield is 3.8 ng (5% PEG 8000).

DESCRIPTION

The problem of concatemerization was resolved by the use of a site-specific nucleic acid cleaving enzyme that targets a site at the 5' end of the TSO. Template-switching is described in FIG. 1.

The entire template-switching reaction described herein can optionally be carried out in a single reaction vessel containing enriched template RNA or cell lysate. This avoids any unnecessary loss of material. One or more of the reagents or the template RNA in the reaction vessel may be free in liquid form (such as free in solution) or may be immobilized on a solid support. For example, optionally, any one or more of the template RNA, the adapter oligo-dT and/or the TSO may be immobilized. In one aspect, the cDNA product is immobilized. Immobilization of the cDNA product of the reverse transcriptase/template-switching is one approach to preventing carryover between reaction steps where the RNA-Seq procedure is performed in two consecutive steps; i.e., reverse transcription and template-switching; and amplification such as PCR for sequencing the amplicon. All or part of a cDNA amplicon can be amplified as desired.

The template-switching reaction involving a site-specific nucleic acid cleaving enzyme may include a label such as a tag or reporter for tracking the completion of concatemer cleavage. Such label may include any molecule that is used by those of ordinary skill in the art to track a DNA dependent reaction (reporter) or immobilize or amplify a DNA dependent reaction (tag). One example of a reporter is a quenching label so that on cleavage, a fluorescent signal occurs which otherwise is quenched by the close proximity of two oligonucleotides. One example of a tag is an aptamer or a biotin molecule or functionally similar molecule that can be used to react with a substrate for immobilizing the cDNA. Optionally, labeling may occur via an agent for immobilizing any one or more of the reagents or products of the reaction as described above.

Reverse transcriptases for use in template-switching include: retroviral reverse transcriptase, retrotransposon reverse transcriptase, retroplasmid reverse transcriptases, retron reverse transcriptases, bacterial reverse transcriptases, group II intron-derived reverse transcriptase, and mutants, variant derivatives, or functional fragments thereof. For example, the reverse transcriptase may be a viral reverse transcriptase, such as M-MLV RT; or the reverse transcriptase may be an invertebrate reverse transcriptase, for example, a *Bombyx mori* reverse transcriptase (e.g., *Bombyx mori* R2 non-LTR element reverse transcriptase). In one aspect, the reverse transcriptase is a variant M-MLV RT that has reduced RNaseH activity as compared to a wild-type M-MLV RT. Polymerases capable of template-switching that find use in practicing the subject methods are commercially available and include a reverse transcriptase commercially available from New England Biolabs, Ipswich, Mass. such as ProtoScript® II or Luna™ or a reverse transcriptase commercially available from Life Technologies, Carlsbad, Calif. (SuperScript® II, III, or IV) or SMARTscribe™ (Takara Bio, Mountain View, Calif.) or Maxima H Minus™ reverse transcriptase (Thermo Fisher Scientific, Waltham, Mass.). In certain aspects, a mix of two or more different polymerases or reverse transcriptases are added to the reaction mixture, e.g., for improved processivity, proof-reading, and/or the like (US 2014/0113332, U.S. Pat. No. 9,012,183, Enyeart, et al., Mobile DNA, 5:2 (2014), WO 2014/201273, US 2015/0111789).

DNA cleavage enzymes used herein are intended to cleave both strands of a double stranded nucleic acid. Examples include: site-specific endonucleases such as restriction endonucleases and homing endonucleases; and/or guided nucleases such as cas nucleases, argonaute, dicer, talens, DNA glycosylases, DNA lyases, structure specific nucleases, or orthologs thereof.

Restriction enzymes with efficient kinetics at 42° C. or above, include: ApeKI, ApoI, BclI, BfuAI, BsaBI, BsaJI, BsaWI, BsiEI, BsiHKAI, BsiWI, BslI, BsmAI, BsmBI, BsmFI, BsmI, BspQI, BsrDI, BsrI, BssHII, BssKI, BstAPI, BstBI, BstEII, BstNI, BstUI, BstYI, BtgZI, BtsCI, BtsI, BtsMutI, FatI, FauI, MwoI, Nb. BsmI, Nb.BsrDI, Nt.BspQI, Nt.BstNBI, PhoI, PI-PspI, PspGI, SfiI, SmlI, TaqI, TfiI, TliI, TseI, Tsp45I, Tsp509I, TspMI, TspRI, Tth111I.

Restriction enzymes with efficient kinetics at 35° C. additionally include: AatII, AccI, Acc65I, AciI, AclI, AcuI, AfeI, AflII, AflIII, AgeI, AhdI, AleI, AluI, AlwI, AlwNI, ApaLI, ApeKI, AscI, AseI, AsiSI, AvaI, AvaII, AvrII, BaeGI, BamHI, BanI, BanII, BbsI, BbvI, BbvCI, BccI, BceAI, BcgI, BciVI, BclI, BcoDI, BfaI, BfuCI, BglI, BglII, BmgBI, BmrI, BmtI, BpmI, Bpu10I, BpuEI, BsaAI, BsaXI, BseRI, BseYI, BsgI, BsoBI, Bsp1286I, BspDI, BspEI, BspHI, BspMI, BsrBI, BsrFI, BsrGI, BssSI, BstEII, BstXI, BstZ17I, Bsu36I, BtgI, Cac8I, ClaI, CspCI, CviKI-1, DdeI, DpnI, DpnII, DraI, DraIII, DrdI, EaeI, EagI, EarI, EciI, Eco53KI, EcoNI, EcoO109I, EcoP15I, EcoRI, EcoRV, Fnu4HI, FokI, FseI, FspI, FspEI, HaeII, HaeIII, HgaI, HhaI, HincII, HindIII, HinfI, HinP1I, HpaI, HpaII, HphI, Hpy99I, Hpy166II, Hpy188I, Hpy188III, HpyAV, HpyCH4III, HpyCH4IV, HpyCH4V, KasI, KpnI, LpnPI, MboI, MboII, MfeI, MluI, MluCI, MlyI, MmeI, MnlI, MscI, MseI, MslI, MspI, MspA1I, mspJI, NaeI, NarI, NciI, NcoI, NdeI, NgoMIV, NheI, NlaIII, NlaIV, NmeAIII, NotI, NruI, NsiI, NspI, PacI, PaeR7I, PciI, PflFI, PflMI, PleI, PhoI, PluT1, PmeI, PmlI, PpuMI, PshAI, PsiI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfoI, SgrAI, SnaBI, SpeI, SphI, SspI, StuI, StyI, StyD4I, XbaI, XcmI, XhoI, XmaI, XmnI, ZraI, Nb.BbvCI, Nt.BtsI, Nt.AlwI, Nt.BbvCI, Nt.BsmAI.

The recognition sequences of each of the above restriction enzymes can be found in ReBASE® (New England Biolabs, Ipswich, Mass.) or the New England Biolabs 2015-16 catalog incorporated herein by reference.

Examples of RNA templates include mRNAs which have poly A tails. Other templates may include non-polyadenylated RNA, such as long non-coding RNA, small RNAs, and RNA from exosome. RNA templates also include prokaryotic RNA. These RNAs play important roles during development. Malfunctioning of the regulation of any of these RNA regulations can cause pathological conditions. To sequence these RNAs with template-switching, one can use randomized primer (with adapter sequence) or dA-tailing the poly(A)-minus RNA (Turchinovic, et al., RNA Biology, 11(7): 817-828 (2014)). In one aspect, therefore, the method comprises the initial step of preparing the template RNA by adding a dA-tail to a poly(A)-minus RNA.

TSOs can have one, or two or more, or three or more 3' terminal deoxyribonucleotides or ribonucleotides or a mixture of deoxyribonucleotides and ribonucleotides. These may include a mixture of nucleotides or nucleotide analogues selected from A, G, T, and C. A requirement of these terminal nucleotides is that they are suitable for hybridizing to the one or more non-template nucleotides on the 3' end of the cDNA formed by the reverse transcriptase used in the reaction. Some examples of nucleotide modifications and analogues are methylated bases, locked nucleic acids, peptide nucleic acid, or deoxyinosine. Examples of terminal transferase activities of different reverse transcriptases that add varying nucleotides at the 3' end of the cDNA suitable for template-switching are provided herein by incorporation by reference, for example in Patel, et al., Proc Natl Acad Sci USA, 91(2):549-53 (1994); Golinelli, et al., Virology, 294 (1):122-34 (2002); Zajac, et al., PLOS ONE, 8, 12, e85270 (2013); Chen, et al., Biotechniques, 30(3):574-80, 582 (2001) and in Table 1.

TABLE 1

| RTase | Preferred nt |
|---|---|
| MMLV | $C^3$ |
| HIV-1 | A; A or C |
| HIV-2 | A or C |

As used herein, the term "full-length complementary DNA or cDNA" is defined as a full-length single-stranded (ss) or double-stranded (ds) cDNA(s), or cDNA fragment(s), which contains the complete sequence information of the template RNA.

As used herein, the term "cDNA library" refers to the whole population of ss or ds cDNAs synthesized from template RNA. The cDNA library can be used directly for different applications known in the art such as for amplification and sequencing or it can be cloned into any suitable recombinant cloning vehicle, and a host can be transformed with the cloning vehicle.

Figure 1:
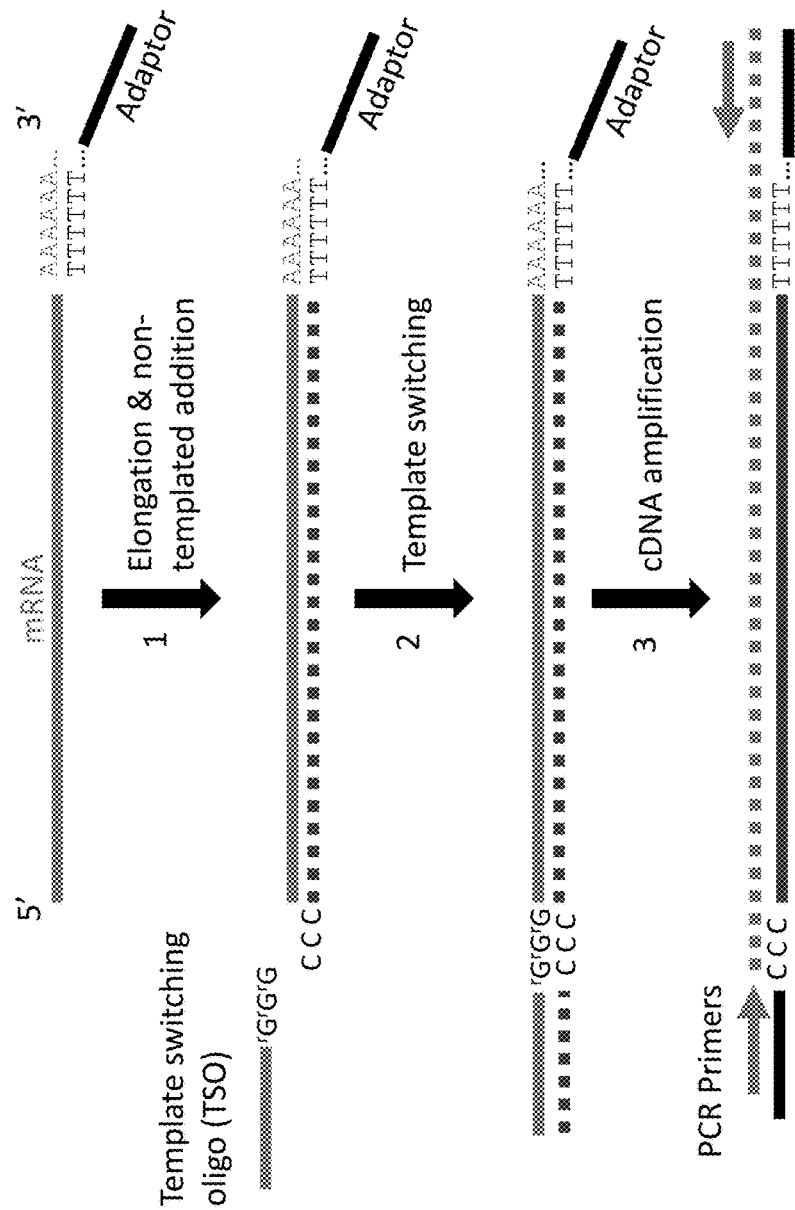
FIG. 1 shows a schematic illustration of RNA library prep using template-switching.

The term "template-switching" reaction refers to a process of template-dependent synthesis of a complementary strand by a DNA polymerase using two templates in consecutive order, wherein the two templates are not covalently linked to each other by phosphodiester bonds. The synthesized complementary strand will be a single continuous strand complementary to both templates. In one example, the first template is polyA+RNA and the second template is a TSO. FIG. 1 shows a template-switching reaction involving a mRNA. An oligo dT with a defined adapter sequence hybridizes to the poly (A) 3' end of the mRNA. This serves as a primer for a reverse transcriptase that copies the mRNA to form a complementary cDNA strand. The reverse transcriptase commonly travels beyond the 5' end of the mRNA to add non-template nucleotides to the 3' end of the cDNA. If a second primer/adapter is present having ribonucleotides or deoxyribonucleotides that are complementary to the non-template nucleotides on the cDNA, the reverse transcriptase will continue to extend the cDNA until the end of this adapter-primer, again adding non template nucleotides at the 3' end.

As used herein, the term "concatemer" refers to a DNA molecule that contains multiple copies of the same DNA sequences linked in series. An example is shown in FIG. 2. The concatemer is made up of multiple copies of TSOs where the 3' end of each TSO hybridizes to non template nucleotides added by the transcriptase as it extends the cDNA by template-switching as described above.

As used herein, the term "site-specific double strand nucleic acid cleaving enzyme" refers to an enzyme that is capable of cleaving both strands of a double stranded nucleic acid in a sequence-specific manner, e.g., a sequence-specific endonuclease. A site-specific double strand nucleic acid cleaving enzyme will cleave both strands of the double stranded form of a TSO if the TSO contains a recognition sequence for that enzyme. This results in a first TSO that is a primer for template-switching being cleaved after template-switching has occurred to separate it from any subsequently formed concatemer. The examples in FIGS. 4-6 show that this is very effective in reducing background caused by various lengths of concatemer otherwise formed by template-switching.

As used herein, the term "RNA:cDNA hybrid" refers to a product after first-strand cDNA synthesis catalyzed by reverse transcriptase using RNA as a template. "RNA-cDNA hybrid" can be full-length if the cDNA portion includes the complete sequence of the 5'-ends of the template mRNA.

As used herein, the term "5' end" refers to any sequence that lies within half of the overall sequence within the 5' portion of the oligonucleotide.

As used herein, the term "reverse transcriptase" is defined as any DNA polymerase possessing reverse transcriptase activity which can be used for first-strand cDNA synthesis of template RNA.

As used herein, two sequences are said to be "complementary" to one another if they are capable of hybridizing to one another to form antiparallel, double-stranded nucleic acid structure.

As used herein, the term "solid support" refers to any known substrate which can be used for the immobilization of a binding ligand or oligonucleotide/polynucleotide sequences by any known method.

As used herein, the term "reporter" refers to any group incorporated into full-length cDNA by conventional chemical or enzymatic labeling procedures and which can be detected by use of conventional techniques, such as scintillation counting, autoradiography, fluorescence measurement, calorimetric measurement, light emission measurement, and other means known in the art. Examples of reporter groups include radioisotopes, fluorescent, chemifluorescent, chemiluminescent, hapten groups, and others known in the art.

As used herein, the term "nucleotide analog" refers to a nucleotide which is not typically found in DNA or RNA and possesses some additional features which can improve efficiency of the template-switching reaction or improve the usage of anchored cDNA generated. For example, suitable nucleotide analogs include modification in the base or sugar-phosphate backbone, like peptide nucleic acid, inosine, 5-nitroindole deoxyribofuranosyl, 5-methyldeoxycytosine, and 5,6-dihydro-5,6-dihydroxydeoxythymidine. Other nucleotide analogs will be evident to those skilled in the art.

As used herein, the term "template" refers to the substrate RNA for the reverse transcriptase to make cDNA. The template RNA is the target in a mixed population of RNA molecules for enrichment.

The term "non-naturally occurring" refers to a composition that does not exist in nature. Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" or "variant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an immunologically tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state. In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

As used herein, the term "oligonucleotide" refers to a multimer of at least 10, e.g., at least 15 or at least 30 nucleotides. In some embodiments, an oligonucleotide may be in the range of 15-200 nucleotides in length, or more. Any oligonucleotide used herein may be composed of G, A, T and C, or bases that are capable of base pairing reliably with a complementary nucleotide. 7-deaza-adenine, 7-deaza-guanine, adenine, guanine, cytosine, thymine, uracil, 2-deaza-2-thio-guanosine, 2-thio-7-deaza-guanosine, 2-thio-adenine, 2-thio-7-deaza-adenine, isoguanine, 7-deaza-guanine, 5,6-dihydrouridine, 5,6-dihydrothymine, xanthine, 7-deaza-xanthine, hypoxanthine, 7-deaza-xanthine, 2,6 diamino-7-deaza purine, 5-methyl-cytosine, 5-propynyl-uridine, 5-propynyl-cytidine, 2-thio-thymine or 2-thio-uridine are examples of such bases, although many others are known. As noted above, an oligonucleotide may be an LNA, a PNA, a UNA, or an morpholino oligomer, for example. The oligonucleotides used herein may contain natural or non-natural nucleotides or linkages.

The term "primer" refers an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Primers are usually single-stranded. Primers have a 3' hydroxyl.

The term "crowding agent" refers to an agent that enhances or facilitates molecular crowding. Crowding agents are believed to bind to and tie up water in a solution, allowing other components of the solution to come into closer contact with one another. Crowding agents include a variety of well-known macromolecules, such as polymers, e.g., polyethylene glycol (PEG); Ficoll, such as Ficoll 70; dextran, such as dextran 70; or the like. In general, when PEG is used, a concentration of about 5% (weight/volume) is optimal. However, the amount of PEG can range, e.g., from about 3 to about 7%. Any suitable size of PEG can be used, e.g., ranging from about PEG-200 (e.g., PEG-400, PEG-600, PEG-1000, PEG-1500, PEG-3350, PEG-4000, PEG-6000, or PEG-8000) to about PEG-30,000, or even higher.

Following are examples which illustrate procedures for practicing the invention. These examples should not be construed as limiting. All percentages are by weight and all solvent mixture proportions are by volume unless otherwise noted. All references cited herein are incorporated by reference.

EXAMPLES

Example 1

Concatemer Reduction Using a Site-Specific Nucleic Acid Cleaving Enzyme

Single cell isolation can be achieved by serial dilution, flow cytometry, micropipetting, laser capture microdissection, etc. In this example, the sample (293T cells) was trypsinized, washed and stored in PBS buffer and then serially diluted to an appropriate concentration so that one drop of PBS contained only one cell. This could be verified by microscopy. Then the individual cell was put into the 1× lysis buffer with RNase Inhibitor (New England Biolabs, Ipswich, Mass.) and was incubated at room temperature for 5 minutes. The total RNA in the lysed cell was then analyzed in the following procedure to generate an RNA library. The background was significantly reduced by the use of a site-specific nucleic acid cleaving enzyme to cleave concatemers formed by the reverse transcriptase template-switching by adding multiple TSO sequences. In this example, either single cultured cells or an equivalent amount of total Universal human reference RNA was analyzed.

10 pg (1 ul) of total RNA from a single cell or total Universal human reference RNA, which is equivalent to one cell RNA content, was first annealed to 1 ul immobilized or free Adapter-Oligo dT primer (10 uM), 1 ul dNTP (New England Biolabs, Ipswich, Mass.), 1 ul $H_2O$ and incubated at 72° C. for 3 minutes. The annealed cooled reaction was incubated with: 0.5 ul of ProtoScript II, 0.25 ul of RNase Inhibitor, 1 ul of BsrDI (New England Biolabs, Ipswich, Mass.), 1 ul of Template switching oligo (100 uM), 50 mM Tris-HCl (pH 8.3@25° C.), 75 mM KCl, and 9 mM $MgCl_2$.

The template-switching reaction was performed at 42° C. for 90 minutes, followed by 72° C. for 10 minutes. After the reaction, 1 ul PCR primer (10 uM) and 2×Q5® master mix (New England Biolabs, Ipswich, Mass.) were added to the reaction to perform PCR: denature at 98° C. for 30 seconds, 18 cycles of 98° C. for 10 seconds, 60° C. for 20 seconds and 72° C. for 4 minutes followed by 72° C. for 10 minutes. The PCR reaction was then purified via AM Pure® Beads (Beckman Coulter, Brea, Calif.). The entire reaction was performed in a single reaction vessel.

The sample was analyzed by digital electrophoresis using a BioAnalyzer 2100. 1 ul of the RNA library was loaded to the High Sensitivity DNA chip (Agilent, Santa Clara, Calif.) in the Bioanalyzer. The results are shown in FIGS. 4-6. The background was significantly reduced in the presence of the site-specific nucleic acid cleaving enzyme due to reduction of concatemer formation.

Example 2

Use of a Crowding Agent with a Site-Specific Nucleic Acid Cleaving Enzyme to Reduce Background Signal 10 pg (1 ul) of total RNA (Universal human reference RNA, Santa Clara, Calif., #740000) was first annealed with 1 ul Adapter-Oligo dT primer (10 uM), 1 ul dNTP (NEB, Ipswich, Mass., #N0447), 1 ul $H_2O$ at 72° C. for 3 minutes followed by 4° C. Then, the annealed mix was incubated with the following components: 0.5 ul of ProtoScript II, 0.25 ul of RNase Inhibitor, 1 ul of BsrDI, 1 ul of template-switching oligo (100 uM), 50 mM Tris-HCl (pH 8.3@25° C.), 75 mM KCl, 9 mM MgCl$_2$, 2.5 mM TCEP and 5% PEG. The template-switching reaction was performed at 42° C. for 90 minutes, followed by 72° C. for 10 minutes. After the reaction, 1 ul PCR primer (10 uM) and 2×Q5 master mix were added to the reaction to perform PCR: denature at 98° C. for 30 seconds, 18 cycles of 98° C. for 10 seconds, 60° C. for 20 seconds and 72° C. for 4 minutes followed by 72° C. for 10 minutes. The PCR reaction was then purified via Ampure Beads. As shown in the FIG. 8, PEG enhance the library yield.

What is claimed is:

1. A composition comprising:
   (a) a reverse transcriptase;
   (b) a template-switching oligonucleotide comprising a recognition sequence for a site-specific double strand nucleic acid cleaving enzyme, wherein the template-switching oligonucleotide has at its 3' end at least one nucleotide that can hybridize to one or more non-templated nucleotides added to a templated cDNA strand by the reverse transcriptase; and
   (c) a site-specific double strand nucleic acid cleaving enzyme that recognizes the recognition sequence in the template-switching oligonucleotide.

2. The composition of claim 1, further comprising a RNA template.

3. The composition of claim 2, wherein the RNA template is total RNA or polyA$^+$RNA.

4. The composition of claim 2, wherein the RNA template is RNA from a mammal.

5. The composition of claim 2, wherein the RNA template comprises a 5' modified GMP cap.

6. The composition of claim 5, wherein the 5' modified GMP cap is a 7-methylguanosine or an affinity tag-labeled GMP cap.

7. The composition of claim 1, further comprising a cDNA synthesis primer which is an oligo(dT) primer, a random primer, or a transcript-specific primer.

8. The composition of claim 1, further comprising a cDNA synthesis primer having a 5' tail that does not hybridize to the RNA template.

9. The composition of claim 1, wherein the template-switching oligonucleotide is a DNA-RNA chimera.

10. The composition of claim 1, wherein the template-switching oligonucleotide comprises an amplification primer sequence, and optionally a molecular barcode sequence, between the recognition sequence for the site-specific nucleic acid cleaving enzyme and the at least one or more nucleotides at its 3' end for hybridizing to non-template nucleotides at the 3' end of the cDNA strand.

11. The composition of claim 1, wherein the template-switching oligonucleotide comprises three riboguanine residues at its 3' end.

12. The composition of claim 1, wherein the reverse transcriptase is Molatney murine leukemia virus (M-MLV), M-MtV reverse transcriptase lacking RNaseH activity, human T-cell leukemia virus type I (HTLV-I) reverse transcriptase, bovine leukemia virus (BIN) reverse transcriptase, Rous sarcoma virus (RSV) reverse transcriptase, or human immunodeficiency virus (HIV) reverse transcriptase, or a variant thereof.

13. The composition of claim 1, wherein the site-specific double strand nucleic acid cleaving enzyme is a restriction endonuclease.

14. The composition of claim 1, wherein the restriction endonuclease is active at a temperature in the range of 40° C. to 55° C.

15. The composition of claim 1, wherein the site-specific double strand nucleic acid cleaving enzyme is an N-glycosylase.

16. The composition of claim 1, wherein the site-specific double strand nucleic acid cleaving enzyme is a lyase (N-glycosylase-lyase).

17. The composition of claim 1, wherein the site-specific double strand nucleic acid cleaving enzyme is an endonuclease.

18. The composition of claim 1, wherein the site-specific double strand nucleic acid cleaving enzyme is a cas9 ortholog.

19. The composition of claim 1, wherein the site-specific double strand nucleic acid cleaving enzyme is an Argonaut ortholog.

20. The composition of claim 14, wherein the restriction endonuclease is capable of inactivation by incubation at a temperature of at least 65° C. for a period of 10 minutes.

21. A method for making cDNA comprising:
   (a) obtaining a reaction mix comprising the composition of claim 1, a cDNA synthesis primer and an RNA template; and
   (b) incubating the reaction mix so as to produce cDNA molecules that comprise, at the 3' end, an added sequence comprising the complement of a sequence at the 5' end of the template-switching oligonucleotide;
      wherein, during the incubation of (b), the site-specific double stranded nucleic acid cleaving enzyme prevents concatamers of the double stranded form of the template-switching oligonucleotide at the 3' end of the cDNA molecules.

22. The method of claim 21, wherein step (b) comprises incubating the reaction mix at a temperature of 35° C. to 55° C. for a period of at least 30 minutes.

23. The method of claim 21, further comprising, after step (b), inactivating the reverse transcriptase and the site-specific nucleic acid cleaving enzyme by incubating the reaction mix at a temperature of at least 65° C. for a period of at least 10 minutes.

24. The method of claim 21, further comprising: (c) amplifying the cDNA molecules to produce amplification products.

25. The method of claim 24, wherein (c) is performed using a first primer and a second primer, wherein the first primer hybridizes to the added sequence at the 3' end of the cDNA and the second primer hybridizes to the complement of a sequence in the cDNA synthesis primer; and wherein the amplification is performed by PCR.

26. The method of claim 21, wherein the method further comprises sequencing the amplification products.

27. The method of claim 21, wherein the RNA template is from a clinical sample.

28. The method according to claim 21, wherein the reaction mix comprises a crowding agent.

29. The method according to claim 28, wherein the crowding reagent is polyethylene glycol.

30. The composition of claim 1, comprising a crowding agent.

31. The composition and methods according to claim 30, wherein the crowding agent is polyethylene glycol.

* * * * *